United States Patent [19]

Lapidot

[11] 3,940,993
[45] Mar. 2, 1976

[54] PROPORTIONAL FLUID SAMPLING DEVICE

[75] Inventor: Heine Lapidot, Latham, N.Y.

[73] Assignee: General Electric Company, Waterford, N.Y.

[22] Filed: Dec. 19, 1974

[21] Appl. No.: 534,377

[52] U.S. Cl. .............................. 73/421 B; 73/422 R
[51] Int. Cl.² .......................................... G01N 1/14
[58] Field of Search ....................... 73/421 B, 422 R

[56] References Cited
UNITED STATES PATENTS

| | | | |
|---|---|---|---|
| 3,727,464 | 4/1973 | Rutkowski et al. | 73/421 B |
| 3,811,324 | 5/1974 | Doncer et al. | 73/421 B |

Primary Examiner—Richard C. Queisser
Assistant Examiner—Marcus S. Rasco
Attorney, Agent, or Firm—John L. Young; E. Philip Koltos; Edward A. Hedman

[57] ABSTRACT

An apparatus is disclosed for obtaining from a fluid stream, a sample having a volume that is proportional to the flow rate of the fluid stream. The apparatus comprises intake means for withdrawing fluid material from a stream; a sampling reservoir having a conduit inlet at the top and an outlet at the bottom; an equalizer chamber in communication with said sampling reservoir, said equalizer chamber being operated in conjunction with a gas bubbling system to maintain the level of liquid in said sampling reservoir so that the volume of said liquid is proportional to the flow rate in said fluid stream.

4 Claims, 1 Drawing Figure

PROPORTIONAL FLUID SAMPLING DEVICE

This invention provides a novel apparatus for obtaining a sample from a fluid stream that is proportional to the flow rate of the fluid stream. The elements of the apparatus comprise intake means for withdrawing fluid material from a stream; a sampling reservoir having a conduit inlet at the top and an outlet at the bottom; an equalizer chamber in communication with said sampling reservoir, said equalizer chamber being operated in conjunction with a gas bubbling system to maintain the level of liquid in said sampling reservoir so that the volume of said liquid is proportional to the flow rate in said fluid stream.

BRIEF DESCRIPTION OF THE DRAWING

The drawing is a schematic which illustrates the apparatus of the invention.

BACKGROUND OF THE INVENTION

Figure 1:
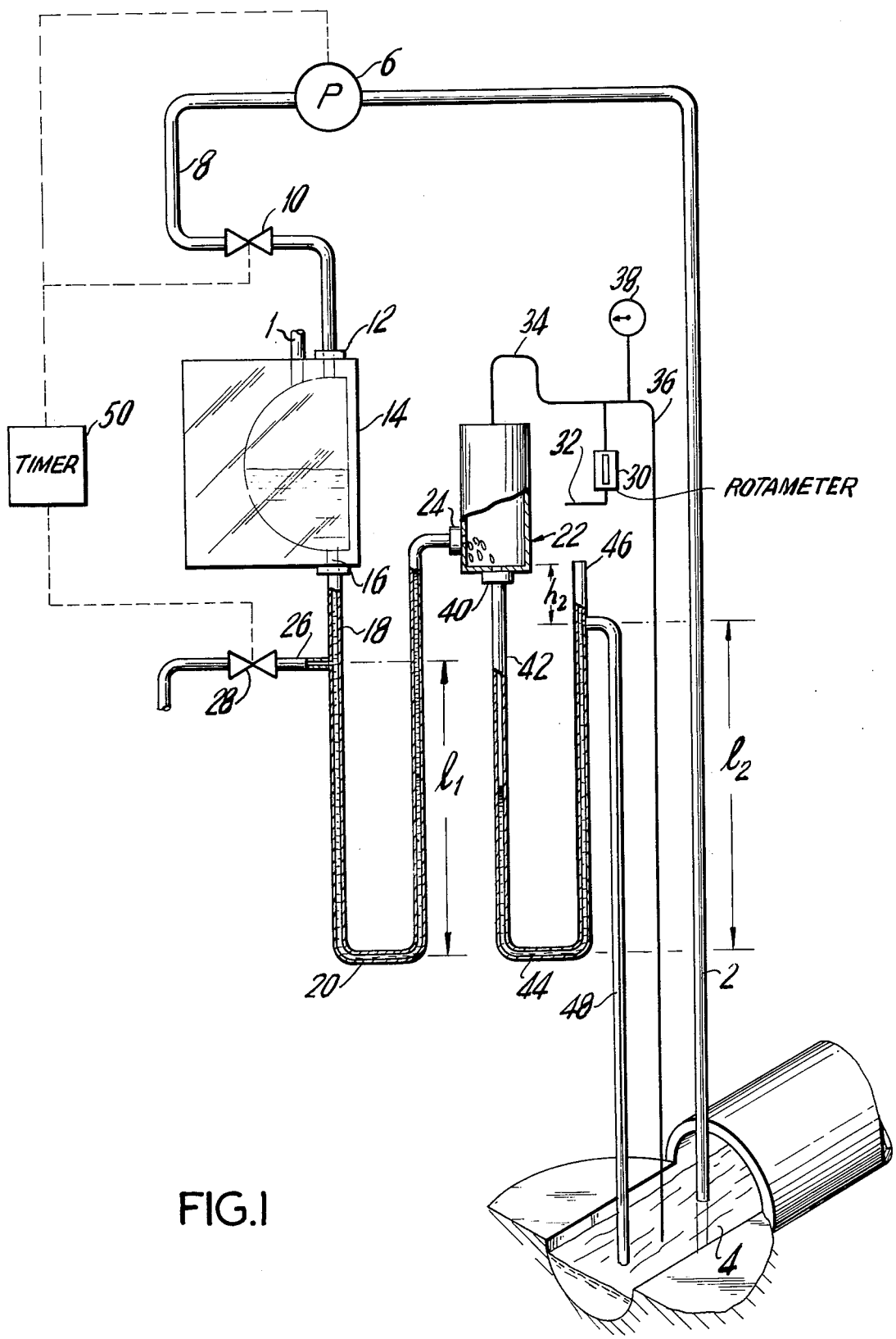

A fundamental operation in essentially all water pollution abatement programs is the monitoring of the pollution loads that are imposed on the sewer network. This is especially important in the case of the control of pollution that is caused by the effluent from industrial plants. The pollution load is obtained by measuring over a period of time, typically 24 hours, two parameters, namely the concentration of the pollutant and the flow rate of the stream. The concentration of the pollutant is measured by analysis of a sample drawn from the stream during the timed interval. However, in order to obtain a representative sample of a fluid stream, the sample must be withdrawn at a rate that is proportional to the flow rate of the stream. The prior art sampling devices draw either a constant rate sample thus producing a less representative sample because of lack of proportionality to the stream flow rate, or provide a proportional sample by combining flow metering and timing devices with the basic sampling device. These devices are rather complex and expensive. Also, operational difficulties are encountered when corrosive or sticky fluids are being monitored.

The present invention provides an apparatus that eliminates the need to know the flow rate, but provides a sample volume proportional to the flow rate.

Accordingly, it is a primary object of this invention to provide an apparatus for obtaining from a fluid stream a sample that is proportional to the flow rate of that stream. In addition, an added advantage of the apparatus is that the total volume of sample collected over a period of time is proportional to the total amount of water that went past the sampling point in the sewer; the apparatus may be adapted to act as a totalizer.

DESCRIPTION OF THE INVENTION

The apparatus of the invention which is intended to be used in obtaining from a flowing stream of fluid material, a sample of said fluid material having a volume that is proportional to the flow rate comprises:

a. intake means for withdrawing fluid material from a stream of fluid material and passing said fluid to a sampling reservoir;

b. a sampling reservoir comprising a chamber;

c. an upper conduit inlet at the top of said sampling reservoir and a lower conduit outlet at the bottom of said sampling reservoir;

d. a drain conduit connected to said lower conduit outlet of said sampling reservoir, said conduit being extended in a first downward direction and in a second upward direction to form a first hydraulic seal means, said lower conduit having outlet means for withdrawal of fluid from said sampling reservoir;

e. an equalizer chamber in open communication with said hydraulic seal means at the same level as said conduit outlet;

f. a gas bubbling system in open communication with a conduit means at the top of said equalizer chamber and bubbling gas at the open end of another conduit that is submerged in said stream for measuring the variations in the depth of fluid in said stream; and g. an outlet means at the bottom of said equalizer chamber below the level at which said first hydraulic seal means is in open communication with said equalizer chamber, said outlet means being connected to an equalizer chamber drain that extends in a first downward direction and in a second upward direction to form a second hydraulic seal means that is connected to a discharge line.

The intake means for withdrawing fluid material from the stream of fluid material may comprise a pump having an intake conduit in communication with the fluid stream from which the sample is to be withdrawn. The output of the pump is connected to a pump discharge conduit that is connected to the upper conduit inlet. The pump discharge conduit is preferably provided with a valve which may be closed to cut off the intake of fluid into the sampling reservoir. The drain conduit at the bottom of said sampling reservoir is in communication with a valved sample withdrawal conduit for withdrawal of fluid from said sampling reservoir. The above-mentioned valves may be operated manually or by remote control. The preferred method is to have a remote control means that will cause the valve in the pump discharge conduit to close at the same time the valve in sample withdrawal conduit is opened. The valves may be operated by any convenient method such as by air, electric motors or by solenoids. The remote control means may include timing means that may be set to withdraw samples at predetermined intervals.

The equalizer chamber may be constructed in any desired configuration provided that the inlet from the first hydraulic seal is above the outlet means at the bottom of said equalizer chamber and at the same level as the lower conduit outlet of the sampling reservoir. Also, the conduit from the gas bubbling system must be connected to the equalizer chamber above the inlet from the first hydraulic seal. The connection with the gas bubbling system provides a static gas pressure which will change to reflect changes in the flow of fluid in the stream. This change in the static gas pressure will act through the equalizer chamber to cause the volume of liquid in the sampling reservoir to reflect the flow rate of the fluid stream that is being monitored. The equalilzer chamber may be constructed in almost any configuration such as cylindrical, spherical or cubical. The essential requirement for the equalizer chamber is the location of the conduit which must be placed so that the equalizer chamber can effectively exert pressure changes to vary the level of fluid in the sampling reservoir. The gas bubbling system operates by passing air or another gas through a conduit submerged in the flowing stream. That conduit is also connected to the equalizer chamber with an outlet conduit so that a backpressure is exerted which varies with the flow rate as shown by variations in the level of fluid. Control means are provided to vary the gas flow rate. A rotameter may be used in a gas bubbling system by passing a gas through the rotameter and then through a rotameter outlet conduit which has its end submerged in the fluid stream which is to be monitored. The higher the level of the fluid, the greater will be the backpressure or resistance to the air which is passed through the rotameter. The rotameter outlet conduit is in open communication with the equalizer chamber where the backpressure acts on the fluid to cause the level of fluid in the sample reservoir to vary directly with the level of liquid in the sewer which is a function of the flow rate of liquid in the sewer.

The sampling reservoir may be constructed of opaque or translucent materials in almost any configuration. If desired, the sampling reservoir may be constructed with translucent materials in a configuration which duplicates the configuration of a sewer pipe. This may be calibrated to permit the taking of visual readings of the flow rate. Since the flow rate in sewers is a function of the depth of fluid in the pipe, by constructing a sample reservoir in a specific shape, any mathematical function of depth can be closely approximated. The volume of sample collected in such a reservoir follows the same function of depth as the sewer flow rate, therefore, making the sample volume proportional to the flow rate.

DESCRIPTION OF THE PREFERRED EMBODIMENT

FIG. 1 shows a schematic outline to illustrate a preferred apparatus according to the present invention. The intake conduit 2 is shown submerged in the flowing stream of effluent 4. The placement of the intake conduit 2 is not critical and it may be remote from the location where the sampling reservoir is maintained. The intake conduit 2 is connected with pump 6 which passes fluid material to the pump discharge conduit 8. The fluid material is then passed through a solenoid operated valve 10 to the upper conduit inlet 12 of sample reservoir 14 which is open to the atmosphere at venting point 1. At the bottom of sample reservoir 14 is the lower conduit outlet 16 to which is connected drain conduit 18. The drain conduit 18 is formed into first hydraulic seal 20 which is in open communication with equalizer chamber 22 at inlet 24. The drain conduit 18 is in open communication with valved sample withdrawal conduit 26 which has a solenoid operated valve 28.

Inlet 24 to equalizer chamber 22 is at the same level as conduit outlet 16. Rotameter 30 has an air inlet line 32 and is in open communication with equalizer chamber 22 through the conduit 34 that is connected to the top of the equalizer chamber. The rotameter is also in open communication with the fluid flowing in the stream 4 through conduit 36. Conduit 36 ends in an open end that is submerged in the stream and is as close as possible to the bottom of the sewer pipe. The air or gas bubbles freely out of this open end. Optionally, a direct reading gauge 38 may be employed to provide a visual means of reflecting the actual level of the fluid in stream 4. The equalizer chamber 22 is provided with outlet means 40 that is connected to equalizer drain 42 which is formed into hydraulic seal 44. The second hydraulic seal 44 is provided with air vent 46 to prevent the formation of a vacuum and is connected to discharge line 48 which is a return line to the sewer for excess liquid.

The connection to discharge line 48 is located a vertical distance $h_2$ below outlet means 40 of equalizer chamber 22. Typically, $h_2$ is generally 3 to 5 inches but can be any distance below outlet means 40.

Both hydraulic seals, 20 and 44, have a length $l$ and $l_2$ at least equal to the diameter of the sewer pipe to ensure that the hydraulic seal is maintained through the entire range of operation.

Optionally, automatic timer 50 may be connected to valves 10 and 28 to close valve 10 and open valve 28 for 20–30 seconds at intervals of 5–15 minutes to provide a proportional sample of the fluid material. Also, the timer may optionally be used to shut off pump 6 when a sample is taken.

Obviously, other modifications and variations of the present invention are possible in the light of the above teachings. It is, therefore, to be understood that changes may be made in the particular embodiments of the invention described which are within the full intended scope of the invention as defined by the appended claims.

I claim:

1. An apparatus for obtaining from a flowing stream of fluid material, a sample of said fluid material having a volume that is proportional to the flow rate, said apparatus comprising:
    a. intake means for withdrawing fluid material from a stream of fluid material and passing said fluid to a sampling reservoir;
    b. a sampling reservoir comprising a chamber;
    c. an upper conduit inlet at the top of said sampling reservoir and a lower conduit outlet at the bottom of said sampling reservoir;
    d. a drain conduit connected to the said lower conduit outlet of said sampling reservoir, said conduit being extended in a first downward direction and in a second upward direction to form a first hydraulic seal means said lower conduit having outlet means for withdrawal of fluid from said sampling reservoir;
    e. an equalizer chamber in open communication with said first hydraulic seal means at the same level as said conduit outlet;
    f. a gas bubbling system in open communication with a conduit means at the top of said equalizer chamber and bubbling gas at the open end of another conduit that is submerged in said stream for measuring the variation in the depth in said stream; and
    g. an outlet means at the bottom of said equalizer chamber below the level at which said first hydraulic seal means is in open communication with said equalizer chamber, said outlet means being connected to an equalizer chamber drain that extends in a first downward direction and in a second upward direction to form a second hydraulic seal means that is connected to a discharge line.

2. An apparatus as defined in claim 1 wherein said intake means for withdrawing fluid material and passing said fluid to a sampling reservoir comprises a pump and an intake and a discharge conduit.

3. An apparatus as defined in claim 1 wherein said conduit outlet at the bottom of said sampling reservoir is in communication with a valve controlled conduit for withdrawal of a fluid sample from said sampling reservoir.

4. An apparatus as defined in claim 2 wherein said discharge conduit includes valve means.

* * * * *